United States Patent
Andreasen et al.

(10) Patent No.: US 6,977,249 B1
(45) Date of Patent: Dec. 20, 2005

(54) PROCESS FOR PRODUCING AN IRON-DEXTRAN COMPOUND, IRON-DEXTRAN COMPOUND PRODUCED ACCORDING TO SAID PROCESS, PHARMACEUTICAL COMPOSITION FOR PROPHYLAXIS OR TREATMENT OF IRON-DEFICIENCY AND USE OF SAID COMPOUND FOR THE PREPARATION OF PARENTERALLY ADMINISTRABLE PHARMACEUTICAL COMPOSITION

(75) Inventors: Hans Berg Andreasen, Viby Sjælland (DK); Lars Christensen, Roskilde (DK)

(73) Assignee: Pharmacosmos Holding A/S, Rosklide (DE)

( * ) Notice: Subject to any disclaimer, the term of this patent is extended or adjusted under 35 U.S.C. 154(b) by 0 days.

(21) Appl. No.: 09/509,681

(22) PCT Filed: Jul. 29, 1999

(86) PCT No.: PCT/DK99/00425

§ 371 (c)(1),
(2), (4) Date: Mar. 30, 2000

(87) PCT Pub. No.: WO00/30657

PCT Pub. Date: Jun. 2, 2000

(30) Foreign Application Priority Data

Nov. 20, 1998 (DK) ................................ 1998 01526

(51) Int. Cl.[7] .................. A61K 31/721; A61K 31/715; A61K 31/70
(52) U.S. Cl. .............................. 514/59; 514/54; 514/23
(58) Field of Search ................................ 424/400, 422; 514/59, 112, 124, 54, 23; 536/112, 113, 114, 536/124

(56) References Cited

U.S. PATENT DOCUMENTS

| RE24,642 E | 4/1959 | London et al. ............... 167/68 |
| 2,885,393 A | 5/1959 | Herb ........................... 260/209 |
| 3,093,545 A | 6/1963 | Westfall et al. ............... 167/68 |
| 3,234,209 A | 2/1966 | Floramo ...................... 260/209 |
| 3,549,614 A * | 12/1970 | Mioduszewski et al. ..... 536/113 |
| 3,697,502 A | 10/1972 | Christensen ................. 260/209 |
| 4,370,476 A * | 1/1983 | Usher et al. ................. 536/113 |
| 4,827,945 A | 5/1989 | Groman et al. ............. 128/653 |
| 5,102,652 A | 4/1992 | Groman et al. ................. 424/9 |
| 5,624,668 A | 4/1997 | Lawrence et al. ............. 424/78 |
| 6,291,440 B1 * | 9/2001 | Andreasen et al. ........... 514/59 |

FOREIGN PATENT DOCUMENTS

| DK | 117730 | 3/1960 | .......... A61K 27/06 |
| DK | 129942 | 10/1967 | .......... C08B 19/08 |
| DK | 129353 | 5/1968 | .......... C08B 19/08 |
| DK | 122398 | 7/1968 | .......... C08B 19/08 |
| DK | 0420/98 | 3/1998 | |
| EP | 0 150 085 A2 | 7/1985 | .......... C08B 37/02 |
| EP | 634174 A1 | 1/1995 | .......... A61K 31/70 |
| GB | 1200902 | 8/1970 | .......... C08B 19/08 |
| HU | 176 073 B | 12/1980 | |
| HU | P0101189 | 8/2001 | |
| NZ | 150358 | 3/1970 | |
| NZ | 150980 | 2/1971 | |
| WO | WO 97/17377 | 5/1997 | .......... C08B 37/02 |

* cited by examiner

Primary Examiner—Thurman K. Page
Assistant Examiner—Simon J. Oh
(74) Attorney, Agent, or Firm—Sughrue Mion, PLLC

(57) ABSTRACT

In a process for producing an iron-dextran compound for use in parenteral treatment of iron-deficiency in humans or animals a stable compound of desired relatively low molecular weight is obtained by using first hydrogenation and then oxidation to convert reducing terminal groups on the dextran molecules before reaction with the iron. By varying the ratio of hydrogenated groups to oxygenated groups the average molecular weight of the resulting iron-dextran compound can be varied.

28 Claims, No Drawings

//PROCESS FOR PRODUCING AN IRON-DEXTRAN COMPOUND, IRON-DEXTRAN COMPOUND PRODUCED ACCORDING TO SAID PROCESS, PHARMACEUTICAL COMPOSITION FOR PROPHYLAXIS OR TREATMENT OF IRON-DEFICIENCY AND USE OF SAID COMPOUND FOR THE PREPARATION OF PARENTERALLY ADMINISTRABLE PHARMACEUTICAL COMPOSITION

BACKGROUND OF THE INVENTION AND PRIOR ART

Iron-deficiency anemia has been described as one of the most common—possibly the most common—pathological conditions among humans when viewed on a global basis. Also in modern farm-breeding of pigs and other domestic animals iron-deficiency anemia is a problem unless suitable prophylactic measures are taken.

Although iron-deficiency anemia can often be pre-vented or cured by oral administration of iron-containing preparations, it is in many cases preferred to use parenterally administrable iron preparations to avoid variations in bioavailability of oral administrations and to ensure effective administration.

Therefore, iron-containing preparations for parenteral use, i.e. subcutaneous, intramuscular or intravenous administration, have for many years been at the disposal of the veterinary or human medical practitioner.

Various iron-containing substances have been used or suggested as components in parenterally injectable preparations against iron-deficiency anemia, such as saccharated ferric oxide. However, the most common preparations accepted today are such which comprise a combined product of ferric oxyhydroxide (or ferric hydroxide) in association with dextran since such preparations are less toxic than for instance the ferric saccharates. Dextran is a polymeric carbohydrate produced by the microorganisms *Leuconostoc mesenteroides*.

An iron-containing preparation for parenteral injection should obviously satisfy several requirements including ready availability of the iron for haemoglobin synthesis, absence of local or general side-effects and stability on storage enabling a satisfactory shelf-life at ambient temperature.

Iron-dextran preparations for the treatment of anemia have been marketed for decades, and many variations in the manufacturing process and in the selection of starting materials have been suggested with a view to improving the stability of such preparations and to decrease the amount of side effects obtained at their administration.

As examples of patents dealing with these problems the following may be cited:

U.S. Pat. No. 2,885,393 (1959) describes a basical process of producing an iron-dextran complex in which the average molecular weight of the dextran is 30,000 to 80,000 Daltons (Da) or lower. The suitability of these complexes for human therapy does not appear from this patent specification.

U. S. Re. 24,642 (1959) comprises a detailed explanation of the requirements to an iron solution intended for intramuscular injection, incorporated herein by reference. The patent deals with a substantially nonionic complex of ferric hydroxide with a dextran having an average intrinsic viscosity at 25° C. of about 0.025 to about 0.25, as well as a process for preparing such a complex by contacting a dextran as described with ferric hydroxide formed in situ by reaction between a ferric salt and an alkali base. No information as to the desired molecular weight of the dextran is given, and no chemical modification of the dextran, apart from a partial depolymerisation, is suggested.

U.S. Pat. No. 3,093,545 (1963). This patent discloses some details such as temperatures and pH-values in an improved method of preparing a product apparently very similar to the one prepared in the last mentioned above patent.

GB 1,200,902 (1970) teaches that in contrast to preparing the ferric hydroxide in situ it is advantageous to preform the ferric hydroxide under controlled conditions since such ferric hydroxide will readily form complexes with dextrans. It is stated that not only partially depolymerised dextran having a weight average molecular weight in the range of for example 500–50,000 Da, preferably in the range 1,000–10,000 Da, but also modified forms or derivatives of dextran such as hydrogenated dextrans or oxidised dextrans or alkali treated dextrans come into consideration as theoretical possibilities. However, the only dextrans specifically mentioned are oxidized dextrans having an average molecular weight of 3,000 and 5,000 Da, resp. The ferric hydroxide is preprepared before contact with the dextran. This means that the resulting product consists of ferric oxyhydroxide on which the dextran forms a coating in contrast to the more homogeneous products formed by precipitatig the ferric hydroxide in situ, that means in the presence of the dextran.

DK 117,730 (1970) deals with a process in which hydrogenated dextran having a molecular weight between 2,000 and 10,000 Da is reacted with ferric hydroxide in aqueous medium. The average molecular weight of the dextran used in the embodiment examples is not indicated. However, the intrinsic viscosity is stated as approximately 0,05 which could correspond to an average molecular weight of approximately 5,000 Da.

DK 122,398 (1972) also discloses the use of hydrogenated dextran for preparing complex compounds with ferric hydroxide, and it is explained that a substantially lower toxicity is obtained than when non-hydrogenated dextran is used. The subject of the patent is a process in which moist ferric hydroxide is mixed with dry hydrogenated dextran, and after optional addition of citric acid or citrate the mixture is heated and purified.

U.S. Pat. No. 3,697,502 (1972) discloses a process for producing an iron-dextran preparation in which citric acid is added to the dextran and a simultaneous addition of alkali metal hydroxide solution and ferric chloride solution is made. The average molecular weight of the dextran is between 3,000 and 20,000 Da. The dextran used in the embodiment examples has a molecular weight of 7,000 and 10,000 Da, resp.

DK 129,353 (1974) is directed on an analogy process for producing a ferric hydroxide-dextran derivative at an average molecular weight of the dextran of at the most 50,000 Da, and the terminal groups of the polymer chains thereof have been modified to convert the terminal reducing anhydroglucose unit into a corresponding carboxylic acid group. Although the limits indicated for molecular weight of the dextran are very broad, viz. from 500 to 50,000 Da, preferably from 1,000 to 10,000 Da, the only exemplified dextran has an average molecular weight of 5,000 Da.

DK 129,942 (1974) has similarity to the above last-mentioned DK patent and deals with the manufacture of ferric hydroxide complexes with dextran hepton acid or dextrine hepton acid. The hepton acids are prepared by hydrolyzing the corresponding cyanhydrids.

U.S. Pat. No. 4,827,945 (1989) and U.S. Pat. No. 5,102,652 (1992) both deal with superparamagnetic metal oxides such as iron oxides coated with or associated with polymeric materials such as dextran. The polymer is contacted with a mixture of the metal oxides in two different oxidation stages to produce a superparamagnetic combined product which is afterwards oxidized to transform all the metal oxide into the highest of said oxidation steps. The product is especially useful as contrast agent in magnetic resonance imaging in medical diagnosis. However, it is also mentioned that it can be used for treatment of iron-deficiency anemia. The molecular weight of the polymers, including carbohydrates such as dextran, are preferably from 5,000 to 250,000 Da.

In spite of the several attempts to improve iron-dextran preparations for treatment of anemia, as reflected in the above patents, the preparations prepared according to the state of the art still have some drawbacks.

This is a result of the fact that in some patients the preparations may cause delayed hypersensitivity, or severe anaphylactic side effects, resulting e.g. in dyspnea, hypotension, shock and death. Also other toxic reactions might be observed.

Besides, several of the prior art preparations are not able to meet current requirements as to stability. Lacking stability may manifest itself as gelatination of the liquid or precipitation of iron hydroxide or oxyhydroxide.

Moreover, the promoting action of the commercially available iron-dextran preparations on the heamoglobin synthesis in the patients receiving said preparations presents itself rather late after administration, and reestablishment of desired haemoglobin levels takes place more slowly than often desired.

Copending Art

Copending non-published Danish patent application 420/98 (incorporated herein by reference) discloses an invention by means of which certain of the above mentioned drawbacks are overcome. Said invention is based on the recognition that many of the specified drawbacks are associated with the presence of insufficiently hydrolyzed, relatively high-molecular weight dextran in the dextran used as starting material as well as with the presence of low-molecular weight saccharides therein.

This recognition is utilized to produce, i.a. by means of membrane technique, an iron-dextran compound which is characterized in that it comprises hydrogenated dextran having a weight average molecular weight (Mw) between: 700 and 1,400 Da, preferably approximately 1,000 Da, a number average molecular weight (Mn) of 400 to 1,400 Da and wherein 90% by weight of the dextran has molecular weights less than 2,700 Da and the Mw of the 10% by weight fraction of the dextran having the highest molecular weights is below 3,200 Da, in stable association with ferric oxyhydroxide.

SUMMARY OF THE INVENTION

Although the product of the above cited Danish Patent Application 420/98 presents a substantial improvement as to decreased toxic reactions and reduced tendency of causing hypersensitivity or anaphylactic side effects and also involves improvements as to stability, there still is a need for a means of controlling the average molecular weight of the final iron-dextran compound, and thus the availability of the iron for haemoglobin synthesis in the human or animal organism.

If an iron-dextran compound having an iron content of e.g. 15–45% b.w. is prepared using a dextran having a weight average molecular weight of approximately 1,000 Da, in which dextran substantially all reducing aldehyde groups have been hydrogenated to alcohol groups, the apparent peak molecular weight (Mp) will typically be approximately 140,000 Da.

It is desired to be able to produce iron-dextran compounds of lower molecular weight and improved stability, especially to obtain compounds in which the iron is readily available for haemoglobin synthesis in the human or animal organisms.

The present invention is based on the recognition that a stable iron-dextran of relatively low molecular weight may be obtained if the reducing aldehyde groups of the hydrolyzed dextran, before the reaction with the iron component, are only partially hydrogenated into alcohol groups whereas substantially all the remaining aldehyde groups are oxidized into carboxylic groups. The molecular weight of the iron-dextran formed when the dextran has received such a pretreatment is substantially lower than the molecular weight of an iron-dextran produced using a similar hydrolyzed dextran having been pretreated only by a, possibly complete, hydrogenation. By adjusting the ratio of the amount of reducing groups hydrogenated to the amount of reducing groups oxidized, it is possible to influence the average molecular weight of the resulting iron-dextran compound. However, if the proportion of oxidized groups in the dextran is too high the iron-dextran will have insufficient stability. It has turned out that to obtain a stable product, the amount of reducing groups in the dextran before oxidation must not exceed a value corresponding to 15% by weight.

Thus, the present invention deals with a process for producing a stable iron-dextran compound having a relatively low molecular weight and a narrow molecular weight distribution, in which process the molecular weight of a dextran is reduced by hydrolysis, and functional aldehyde terminal groups thereof are converted into alcohol groups by hydrogenation, the hydrogenated dextran as an aqueous solution is combined with at least one water-soluble ferric salt, base is added to the resulting solution to form ferric hydroxide, and the resulting mixture is heated to transform the ferric hydroxide into ferric oxyhydroxide as an association compound with the dextran, which process is characterized in that the hydrogenation is only partial, leaving, however, at the most 15% by weight reducing sugar, calculated on the total amount of carbon hydrates, and said dextran before being combined with the ferric salt, and after being subjected to hydrogenation is subjected to an oxidation, said hydrogenation and oxidation being performed to obtain dextran having substantially all aldehyde groups converted into alcohol and carboxylic groups.

Thus, the hydrogenation is performed before the oxidation as a partial hydrogenation leaving a portion of the aldehyde groups of the dextran unreacted, and the oxidation is performed subsequently to obtain a substantially complete conversion of said portion of aldehyde groups into carboxylic acid groups.

It is believed that by this sequence of the hydrogenation and oxidation an advantageous distribution of the resulting alcohol and carboxylic acid group is obtained, since by performing the hydrogenation as an initial operation, the alcohol forming hydrogenation primarily takes place in those aldehyde groups attached to the relatively low molecular weight dextran molecules, whereas the aldehyde groups on the higher molecular weight dextrans are primarily reacted in the oxidation step which means that the carboxylic acid groups formed by the oxidation will to a large extent be introduced in the dextran of higher molecular weight.

This distribution of the alcohol groups and the carboxylic acid groups on the lower molecular weight fraction and the higher molecular weight fraction, resp., is an advantage because it is to expect that the stability of the resulting product will be better than if the alcohol and carboxylic acid groups were distributed at random, and especially better than if the carboxylic acid groups were primarily present on the lower molecular weight portion of the dextran.

However, this invention is not limited to any specific theory concerning the reason for the satisfactory stability of the product produced by said preferred embodiment.

In relatively low molecular weight dextrans as those primarily coming into consideration according to the present invention the influence of the terminal groups (aldehyde groups hydrogenated into alcohol groups or oxidated into carboxylic acid groups) on the polymer chains is substantially more pronounced than in dextrans of higher molecular weight, since the fraction (on weight basis) of functional terminal groups is higher. Therefore, it is important that the carboxylic acid groups, which otherwise could cause instability, are present on the relative high molecular weight fraction of the dextran molecules.

It is preferred to perform the hydrogenation by means of sodium borohydride in aqueous solution.

The oxidation is preferably performed by means of a hypochlorite, preferably sodium hypochlorite, in basic, aqueous solution.

It is important that an oxydant is used having an oxydative capacity suitable for transforming the aldehyde groups into carboxylic acid groups without attacking other sites of the dextran molecules. By tests based on NMR-analysis of the resulting dextrans it has turned out that sodium hypochlorite is a suitable oxydant in this respect, since it seems that all oxygen atoms introduced by the oxidation are present in the carboxylic acid groups.

The process of the present invention is in principle not limited to the use of dextrans having specific molecular weights and molecular weight distribution, however it is prefered to use a dextran having before the formation of the iron-dextran a molecular weight lower that 7,500 Da. To obtain a product which by overall considerations is regarded as most suitable for treatment of iron-deficiency anemia, an embodiment of the process is preferred which is characterized in that after the hydrolysis but before being combined with the water soluble ferric salt, the dextran is purified by one or more membrane processes using a membrane having a cut-off value suitable for holding back dextran of molecular weight above 2,700 Da, possibly followed by further hydrolysis, and followed by one or more membrane processes using membranes with a cut-off between 340 and 800 Da removing the smaller molecules.

A more specifically preferred embodiment comprises the following terminal steps of the process:
preparing an aqueous solution comprising the purified hydrogenated and oxydized dextran and at least one water-soluble ferric salt;
adjusting the pH of said aqueous solution to a value above 10 by addition of a base;
heating the mixture to a temperature above 100° C. until it turns to a black or dark brown colloidal solution which can be filtered through a 0.45 µm filter; and
further neutralization, purification and stabilization using filtration, heating and membrane processes and addition of one or more stabilizers, and optionally drying the solution to obtain the desired iron-dextran compound as a stable powder. Injection liquids may be produced by redissolving this powder, adjustment of pH, sterilizing by filtration and filling into ampoules or vials. Sterilization may also be accomplished by autoclaving the filled ampoules or vials.

Alternatively the drying operation is omitted, and an injection liquid is produced from the purified solution without intermediate drying thereof.

As explained above, a feature of the invention is the adjustment of the ratio of hydrogenated dextran aldehyde groups to the oxidized aldehyde dextran groups, as well as the total percentage of such groups.

It is essential that substantially all reducing groups in the hydrolysed dextran used as starting material are converted by the hydrogenation or the oxidation. This is because any remaining reducing groups react with the ferric compounds when contacted therewith to form ferro compounds which by parenterally administration are more toxic than ferric compounds.

Thus, a further preferred embodiment of the process of the invention is characterized in that the oxidation of the hydrolyzed and hydrogenated dextran is performed to decrease the content of reducing sugar to not above 4% b.w. The amount of reducing sugar in the hydrolysed dextran before hydrogenation is in no way critical and will typically be in the range 20–50% b.w.

The invention also comprises an iron-dextran compound produced according to the above defined process which compound is characterized in that the apparent peak molecular weight (Mp) thereof is 50,000–150,000 Da, preferably 70,000–130,000 Da, more preferably 80,000–120,000 Da, and its iron content is 15–45% b.w. When an aqueous preparation of such an iron-dextran compound is injected intra-muscularly to a patient suffering from iron-deficiency anemia, a positive influence on the haemoglobin production can be observed earlier than when a corresponding amount of iron is injected in a preparation based on the commercial iron-dextran compounds having an apparent peak molecular weight of not below 150,000 Da.

In the present specification and in the attached claims the indications of molecular weights refer to such weights determined by gel-permeation chromatography.

Stability was evaluated as the absense of visible detrimental changes, such as gel formation or precipitation, of the product after heating to 70° C. or more for 10 min.

The invention further comprises a pharmaceutical composition for prophylaxis or treatment of iron-deficiency by parenteral administration, which composition is characterized in that it comprises a compound as defined above.

Such pharmaceutical composition preferably further comprises a salt of an organic hydroxy acid, preferably selected from citrates and gluconates as stabilizer.

Finally, the invention comprises the use of an iron-dextran compound as defined above for the preparation of a parenterally administerable therapeutical composition for prophylaxis or treatment of iron-deficiency by parenteral administration.

The invention is further illustrated by means of the following non-limiting examples.

EXAMPLE 1

(i) Hydrolysis, Hydrogenation and Oxidation of Dextran
2,522 kg hydrolized dextran collected as permeate from a membrane having a cut-off value <5,000 Da, is hydrolized at pH 1.5 at a temperature of 95° C.

The hydrolysis is monitored chromatographically using gel permeation chromatography (GPC), and is terminated by cooling when the molecular weight of the material being hydrolized is estimated to have achieved the desired value, i.e. a weight average molecular weight of 700–1,400 Da.

By the hydrolysis low molecular weight dextran is produced but also glucose is formed. After cooling and neutralization the amount of glucose and very low molecular weight oligomeres is reduced by membrane processes having a cut-off value of 340–800 Da. After this process, the content of dextran is determined by optical rotation ($\alpha_D^{20}$~200) to be 1,976 kg, and the amount of reducing sugar is determined by use of Somogyi's reagent to be 32.0% b.w.

The reducing capability is first decreased by treatment with sodium borohydride. For 939 kg dextran 18,4 kg sodium borohydride is added at basic pH. By this partial hydrogenation it is expected that among the aldehyde groups which are hydrogenated, those dextrans with relatively low molecular weight preponderate.

After the sodium borohydride treatment, the reducing capability is determined to 6.53% b.w.

Hereafter the solution is neutralized to pH <7.0, and subsequently de-ionized. The average molecular weights and the molecular weight distribution is determined chromatographically.

The chromatography also reveals that 90% by weight of the dextran has molecular weights less than 2,700 Da and that the weight average molecular weight (Mw) of the 10% by weight fraction of the dextran having the highest molecular weights is below 3,200 Da.

Mw is found to be 1,200 and the number average molecular weight (Mn) is 800 Da.

Thereafter oxidation is performed using sodium hypochlorite at pH 9.5 and at 50° C. 1075 l of an aqueous 15% w/v NaOCl solution is added.

After the termination of the oxidation, reducing sugar is determined as 0.9% b.w.

After the oxidation diafiltration is performed against pure water to obtain a specific conductivity of 3 mS/cm. The amount of dextran was at this stage 635 kg. NMR-analysis showed that all double-bonded oxygen atoms were present as carboxylic acid groups.

(ii) Synthesis of Iron-Dextran 300 kg dextran, produced as above, is as an 15% solution mixed with 300 kg $FeCl_3$, $6H_2O$.

To the agitated mixture, 250 kg $Na_2CO_3$ as a saturated aqueous solution is added to obtain pH 3.5, and, thereafter, the pH is raised to 11.5 using 50 liters concentrated aqueous NaOH (27% w/v).

The mixture thus obtained is heated above 100° C. until it turns to a black or dark brown colloidal solution that can be filtered through a 0.45 μm filter. The solution is cooled, neutralized to pH 5.00 using concentrated hydrochloric acid, and filtered. The solution is purified using membrane processes until the chloride content in the solution is less than 0.68% calculated on basis of a solution containing 5% w/v iron.

If the chloride content of the solution is less than desired to obtain an isotonic solution, sodium choride is added and pH is finally adjusted to 5.6 and the solution is filtered through a 0.45 μm (or alternatively a 0.2 μm) membrane filter.

The solution is spray dried and the iron-dextran powder is ready for marketing or for further processing.

As alternative to spray drying, the solution can be used for direct production of injection liquids having an iron content of e.g. 5%, as described above.

When using the iron-dextran powder for producing injection or infusion liquids the powder is re-dissolved in an aqueous medium, the pH is checked, and, if necessary, adjusted, and the solution is filled into ampoules or vials after being sterilized by filtration. Alternatively, the sterilization can take place by autoclaving after filling into ampoules or vials.

EXAMPLE 2

(i) Hydrolysis, Hydrogenation and Oxidation of Dextran

This portion of the synthesis is performed as described under (i) in Example 1 above.

(ii) Synthesis of Iron-Dextran 240 kg of the above mentioned dextran as an 12% solution is mixed with 300 kg $FeCl_3$, $6H_2O$.

To the agitated mixture is added 250 kg $Na_2CO_3$ as a saturated aquous solution to obtain a pH-value of 3.5, and thereafter the pH of the mixture is raised to pH 11.6 using 50 liters concentrated aquous NaOH (27% w/v).

The mixture thus obtained is heated above 100° C. until it turns to a black or dark brown colloidal solution that can be filtered through a 0.45 μm filter. The solution is cooled, neutralized to pH of 5.3 using concentrated hydrochloric acid and filtered. The solution is purified using membrane processes until the chloride content is less than 0.68% calculated on basis of a solution containing 5% w/v iron.

If the solution is at this stage heated to above 100° C. for 2 hours the apparent peak molecular weight (Mp) is found to be 104898 Da after cooling. The solution is stable.

The solution is spray dried and the iron-dextran powder is thus finished.

This powder is suitable for producing a liquid iron-dextran preparation containing approximately 5% w/v iron.

In both examples, the yield of iron-dextran powder is above 95%, calculated on basis of the iron used in the process.

EXAMPLE 3

Further iron-dextran preparations were produced using the procedures similar to the one described in Example 1 and 2. The characteristics of the starting materials, the intermediates and the results are shown in the below table.

TABLE

| Synthesis No. | 1 | 2 | 3 | 4 | 5 |
|---|---|---|---|---|---|
| Mw of hydrolized dextran (Da) | 6200 | 2566 | 1212 | 1212 | 922 |
| Reducing sugars after reduction step | 4.4% b.w. | 14.4% b.w. | 6.5% b.w. | 6.5% b.w. | 8.9% b.w. |
| Reducing sugars after oxidation step | 1.2% b.w. | 3.0% b.w. | 0.9% b.w. | 0.9% b.w. | 1.8% b.w. |
| Used amount of reduced and oxidized dextran | 240 kg | 240 kg | 300 kg | 240 kg | 240 kg |

TABLE-continued

| Synthesis No. | 1 | 2 | 3 | 4 | 5 |
|---|---|---|---|---|---|
| Used amount of FeCl₃, 6H₂O | 300 kg | 300 kg | 300 kg | 300 kg | 300 kg |
| Mp of iron-dextran (Da) | 126,350 | 102,653 | 88,146 | 96,875 | 88,326 |
| Stable | Yes | Yes | Yes | Yes | Yes* |

*Stability test at 70° C. for 10 min.

It is thus possible to produce stable low molecular weight iron-dextran preparations using dextrans hydrogenated and oxidized to various extents within the scope of the invention.

EXAMPLE 4 (COMPARISON EXAMPLE)

604 kg of a dextran with a Mw of 1209 Da and a content of reducing sugars of 26.6% b.w. was, without previous hydrogenation, oxidized by treatment with 1780 l of a 15% (w/v) solution of NaOCl in water at pH 9.5, temperature 50° C. After the oxidation the content of reducing sugars was determined to 0.54%.

Preliminary attempt to synthesize iron-dextran compounds using this oxidized dextran failed because the mixture containing iron and dextran formed a gel even before all the Na₂CO₃ was added. Heating such a gelling solution does not lead to formation of a stable colloidal and filterable solution.

This Example shows that it is essential to decrease the proportion of reducing groups in the dextran by hydrogenation before performing the oxidation.

EXAMPLE 5

An iron-dextran solution was prepared as in Example 2.

After the chloride removing membrane process, the pH was adjusted to 8.5 using 10.5 kg citric acid dissolved in an aqueous sodium hydroxide solution. The solution was then heated to above 100° C. for 2 hours. After cooling, the pH is adjusted to 5.6 using concentrated hydrochloric acid. The solution is adjusted to a concentration corresponding to 5.0 w/v % iron. The apparent peak molecular weight is determined to 111,666 and the compound is stable.

By comparing this Example with the Example 2 it appears that the addition of citrate does not significantly alter the molecular weight of the iron-dextran product.

What is claimed is:

1. A process for producing an iron-dextran compound, in which the molecular weight of a dextran is reduced by hydrolysis, and functional aldehyde terminal groups thereof converted into alcohol groups by hydrogenation; said dextran as an aqueous solution is combined with at least one water-soluble ferric salt; base is added to the resulting solution to form ferric hydroxide, and the resulting mixture is heated to transform the ferric hydroxide into ferric oxyhydroxide as an association compound with the dextran, characterized in that the hydrogenation is only partial, leaving at the most 15% by weight reducing sugar, calculated on the total amount of carbon hydrates, and said dextran before being combined with the ferric salt, and after being subjected to hydrogenation is subjected to an oxidation, said hydrogenation and oxidation being performed to obtain dextran having substantially all aldehyde groups converted into alcohol and carboxylic groups, said so transformed dextran having no functional aldehyde groups or carboxylic acid groups in the intermediate glycosyl groups;
wherein the hydrogenation is performed by means of sodium borohydride in aqueous solution; and
wherein the oxidation is performed by means of a sodium hypochlorite in basic aqueous solution.

2. A process according to claim 1, characterized in that the dextran before being combined with the at least one ferric salt has a weight mean molecular weight less than 7,000 Da.

3. A process according to claim 1, characterized in that after the hydrolysis, but before being combined with the water-soluble ferric salt, the dextran is purified by one or more membrane separations having a cut-off value suitable for holding back dextran molecules above 2,700 Da.

4. A process according to claim 1, characterized in that the dextran molecules have a reducing sugar content not above 4% b.w. after the oxidation.

5. A process according to claim 1, characterized in the following steps:
preparing an aqueous solution comprising the hydrogenated and oxidized dextran and at least one water-soluble ferric salt;
adjusting the pH of said aqueous solution to a value above 10 by addition of a base;
heating the mixture to a temperature above 100° C. until it turns into a black or dark brown collodial solution and is filterable through a 0.45 μm filter; and
purification and stabilization of the solution using filtration, heating and membrane separations and addition of one or more stabilizers.

6. A process according to claim 5, characterized in that the stabilization comprises addition of at least one salt of an organic hydroxy acid.

7. A process for producing a dextran preparation, in which process the molecular weight of a dextran is reduced by hydrolysis, and functional aldehyde terminal groups thereof converted into alcohol groups by hydrogenation; characterized in that the hydrogenation is only partial, leaving at the most 15% by weight reducing sugar, calculated on the total amount of carbon hydrates, and said dextran is subsequently subjected to oxidation, said hydrogenation and oxidation being performed to obtain dextran having substantially all aldehyde groups converted into alcohol and carboxylic groups, and said dextran product having no functional aldehyde groups or functional carboxylic acid groups in the intermediate glycosyl groups;
wherein the hydrogenation is performed by means of sodium borohydride in aqueous solution; and
wherein the oxidation is performed by means of a sodium hypochlorite in basic aqueous solution.

8. Iron-dextran compound produced according to claim 1, characterized in that its apparent peak molecular weight (Mp) is 50,000–150,000 Da and its iron content is 15–45% b.w.

9. Dextran preparation obtainable by a process according to claim 7.

10. Dextran preparation according to claim 9, obtained by a process according to claim 7.

11. A pharmaceutical composition for prophylaxis or treatment of iron-deficiency by parental administration comprising a compound according to claim 8.

12. A pharmaceutical composition according to claim 11, further comprising a salt of an organic hydroxy acid as stabilizer.

13. A method of preparing a parenterally administrable therapeutical composition using an iron-dextran compound according to claim 8 for prophylaxis or treatment of iron-deficiency, said method comprising the following steps:
providing the iron-dextran compound as an aqueous solution; and
sterilizing the composition.

14. A method of producing an iron-dextran compound using a dextran preparation obtainable by the process according to claim 7, in a process, said method comprising the following steps:
mixing the dextran preparation as an aqueous solution with at least one water soluble ferric salt;
heating the mixture to a temperature above 100 C until said mixture turns into a colloidal solution that can be filtered through a 0.45 μm filter; and
purification of the solution.

15. The process for producing a dextran preparation according to claim 7, wherein the dextran has a molecular weight less than 7,000 Daltons.

16. The process for producing a dextran preparation according to claim 15, wherein the dextran is purified by one or more membrane separations having a cut-off value suitable for holding back dextran molecules above 2,700 Daltons.

17. The process for producing a dextran preparation according to claim 16, wherein the process further comprises further hydrolysis, and one or more separations having a cut-off value between 340 and 800 Daltons removing the smaller molecules.

18. The process for producing a dextran preparation according to claim 7, wherein the dextran preparation has a reduced sugar content not above 4% b.w. after the oxidation.

19. The process according to claim 3, followed by further hydrolysis and one or more membrane separations having a cut-off value between 340 and 800 Da removing the smaller molecules.

20. A process according to claim 1, characterized in that the oxidation is performed by means of a sodium hypochlorite in basic aqueous solution.

21. A process according to claim 5, further comprising drying the solution to obtain the desired iron-dextran compound as a stable powder.

22. A process according to claim 5, characterized in that the stabilization comprises addition of at least one salt of an organic hydroxy acid selected from the group comprising citrates and gluconates.

23. A pharmaceutical composition according to claim 11, further comprising a salt of an organic hydroxy acid selected from the group comprising citrates and gluconates as stabilizer.

24. Iron-dextran compound produced according to claim 1, characterized in that its apparent peak molecular weight (Mp) is 70,000–130,000 Da and its iron content is 15–45% b.w.

25. Iron-dextran compound produced according to claim 1, characterized in that its apparent peak molecular weight (Mp) is 80,000–120,000 Da and its iron content is 15–45% b.w.

26. The method according to claim 13, further comprising adding salt of an organic hydroxy acid to said compound.

27. The method according to claim 13, further comprising adjusting the iron content of the compound through the addition of water.

28. The method according to claim 14, further comprising drying the solution to obtain the iron-dextran compound as a stable powder.

\* \* \* \* \*